(12) United States Patent
Yamanaka et al.

(10) Patent No.: US 6,468,251 B1
(45) Date of Patent: Oct. 22, 2002

(54) MIXING/CHARGING PORT FOR MEDICAL TREATMENT

(75) Inventors: Syuichi Yamanaka, Hiroshima (JP); Tadashi Okiyama, Hiroshima (JP); Ryoji Fujii, Hiroshima (JP)

(73) Assignee: Jims Co., Ltd., Hiroshima (JP)

( * ) Notice: Subject to any disclaimer, the term of this patent is extended or adjusted under 35 U.S.C. 154(b) by 0 days.

(21) Appl. No.: 09/529,866

(22) PCT Filed: Oct. 22, 1998

(86) PCT No.: PCT/JP98/04797

§ 371 (c)(1),
(2), (4) Date: Apr. 19, 2000

(87) PCT Pub. No.: WO99/24108

PCT Pub. Date: May 20, 1999

(30) Foreign Application Priority Data

Oct. 23, 1997 (JP) .............................................. 9-290952
Nov. 11, 1997 (JP) .............................................. 9-308864
May 27, 1998 (JP) ............................................ 10-145304

(51) Int. Cl.⁷ ................................................ A61M 5/14
(52) U.S. Cl. ............................ 604/256; 604/86; 604/95
(58) Field of Search .......................... 604/86, 246, 256, 604/82, 83, 87, 88, 89, 90, 91, 167.01, 167.02, 167.03, 167.04, 200, 201, 205, 244, 905; 137/845, 851; 251/149.1

(56) References Cited

U.S. PATENT DOCUMENTS

| 4,013,064 A | 3/1977 | Patel et al. |
| 4,819,684 A | 4/1989 | Zaugg et al. |
| 4,874,369 A | 10/1989 | Kulle et al. |
| 5,100,394 A | 3/1992 | Dudar et al. |
| 5,135,489 A | 8/1992 | Jepson et al. |
| 5,158,554 A | 10/1992 | Jepson et al. |
| 5,167,648 A | 12/1992 | Jepson et al. |
| 5,171,234 A | 12/1992 | Jepson et al. |
| 5,188,620 A | 2/1993 | Jepson et al. |
| 5,211,638 A | 5/1993 | Dudar et al. |
| 5,354,275 A | 10/1994 | Behnke et al. |
| 5,411,499 A | 5/1995 | Dudar et al. |
| 5,474,544 A | 12/1995 | Lynn |
| 5,522,804 A | 6/1996 | Lynn |
| 5,549,569 A | 8/1996 | Lynn et al. |
| 5,549,651 A | 8/1996 | Lynn |
| 5,643,218 A | 7/1997 | Lynn et al. |

FOREIGN PATENT DOCUMENTS

| JP | 49-22472 | 6/1974 |
| JP | 52-4685 | 1/1977 |
| JP | 59-135 | 1/1984 |
| JP | 64-31752 | 2/1989 |
| JP | 3-62113 | 9/1991 |
| JP | 4-502570 | 5/1992 |
| JP | 5-22187 | 6/1993 |
| JP | 9-502636 | 3/1997 |
| JP | 1-9580 | 3/1998 |
| JP | 10-118178 | 5/1998 |
| WO | WO 89/00867 | 2/1989 |
| WO | WO 91/07206 | 5/1991 |
| WO | WO 95/03841 | 2/1995 |
| WO | WO 95/07726 | 3/1995 |

OTHER PUBLICATIONS

Internation Search Report, Feb. 23, 1999.
Nov. 21, 2000 European Search Report for EP 98 95 0355.

Primary Examiner—Brian L. Casler
Assistant Examiner—Mark K. Han
(74) Attorney, Agent, or Firm—Merchant & Gould PC (57) ABSTRACT

A mixing/charging port for medical treatment capable of reliably mixing/charging solutions or collecting the solutions in a medical instrument equipped with a solution feed passage, comprising a disc-like valve (1) having an insertion hole at the center, a cover (2) for restraining the valve (1) by covering at least the upper part of the periphery of the valve (1) with the center on the front surface side of the valve (1) left uncovered, and a round fitting hole (6) formed at the center of the cover (2) as anchor means for anchoring an insertion member to a mixing/charging port, the fitting hole (6) and the insertion member being so fitted to each other as to be capable of anchoring.

20 Claims, 11 Drawing Sheets

MIXING/CHARGING PORT FOR MEDICAL TREATMENT

TECHNICAL FIELD

The present invention relates to a mixing/charging port for a medical treatment, which is mounted on a medical instrument to make it easy and reliable to mix/charge solutions from the outside of a solution feed passage or, contrarily, to collect the solutions from the inside of the solution feed passage.

BACKGROUND ART

In infusing a liquid medicine or transfusing blood into the vessel of a patient, it is often necessary to provide a main solution feed passage with a side-infusing line in order to mix/charge different kinds of liquid medicines or to collect the liquid flowing in the solution feed passage as a sample. Conventionally, in this case, a solution feed passage of an infusion set provided with a rubber mixing/charging port (cock) for piercing by needles is used and solutions are mixed/charged by piercing the mixing/charging port with an injection needle, etc. However, in the conventional method, when piercing the site other than the predetermined piercing site of the mixing/charging port with the needle, the liquid may leak from the site. Another problem is that the injection needle is contaminated due to a working error, etc. In particular, since the mixing/charging port is not designed to hold an injection needle or a syringe at the mixing/charging port, when a liquid medicine continuously is required to be mixed/charged, it is necessary to provide the mixing/charging port with various means for fixing and holding a luer, etc. to be inserted ("an insertion member" will be referred to hereinafter). Thus, it was inconvenient to use such a mixing/charging port. For example, it was necessary to wind a syringe needle base and the mixing/charging port together heavily with a tape so as to be fixed to each other. For another example, it was necessary to use a dropping prevention instrument for the piercing needle or the syringe as is disclosed in, for example, JP 5-22187 U. Furthermore, when the side-infusing is carried out, it may be possible to use a three-way valve besides the mixing/charging port. However, when the three-way valve is used, it is necessary to select liquid passages by a cock, thus complicating the operation. In addition, there was a risk of wrongly selecting liquid passages.

Therefore, recently, the mixing/charging port capable of holding an insertion member has been considered. An example includes a mixing/charging port equipped with a valve which opens when a male luer located at the tip of a syringe is inserted into the mixing/charging port to push the valve and which closes by itself when the luer is pulled out from the mixing/charging port.

However, in such a mixing/charging port, it is necessary to hold a luer at the mixing/charging port regardless of whether the state in which the valve is inserted (i.e., valve opens) or the state in which the valve is pulled out (i.e., valve closes). Therefore, there are the following various problems. More specifically, first, it is necessary to deepen a luer receiving part of the mixing/charging port. In such a shape, the liquid leaking from the valve is difficult to be removed, thus easily becoming unsanitary. Furthermore, in the mixing/charging port having such a deep luer receiving part, there is a possibility that the liquid begins to be mixed/charged in a state in which the luer is not sufficiently inserted into the valve. In this case, when a small amount of liquid medicine is mixed/charged, it may be impossible to administer an effective amount of liquid medicine. Secondly, the structure of the valve becomes complicated, which may lead to increasing cost. Furthermore, as the structure of the valve is more complicated, failures are more likely to occur.

On the other hand, in the conventional simple-structured mixing/charging port (for example, a mixing/charging port merely equipped with a disc-like valve made of an elastic member having a slit), it was difficult to insert a luer of a syringe into the mixing/charging port. If possible, it was difficult to hold the syringe reliably at the mixing/charging port. This is because the conventional disc-like valve is formed of a material having a large elasticity and has a simple structure in which the thick main body is merely provided with a slit, so that the valve is subjected to large resistance when the luer is inserted into the valve, and the valve is largely deformed when the valve holds the luer. However, if the thickness of the elastic member is reduced or a material having a small elastic material is used in order to reduce the resistance when the luer is inserted, the backflow prevention effect of the valve is lowered, which may cause liquid leaking.

It is an object of the present invention to avoid the above-mentioned problems and to provide a simple-structured mixing/charging port, in which an insertion member is easily inserted; which is capable of reliably holding/fixing the insertion member at the mixing/charging port and of securing a passage (between the insertion member and the mixing/charging port) when the insertion member is connected to the mixing/charging port; and which is capable of closing the valve when the insertion member is not connected, thereby preventing the liquid from leaking.

DISCLOSURE OF INVENTION

In order to attain the above-mentioned objects, a mixing/charging port of the present invention includes a disc-like valve having an insertion hole at the center, a seating for supporting the lower part of the periphery of the valve with the center of the rear surface side of the valve unsupported, a cover for restraining the valve by covering at least the upper part of the periphery of the valve with the center on the front surface side of the valve left uncovered, and an anchor means for anchoring an insertion member to the mixing/charging port by using the edge of the cover which inserts an insertion member into an insertion hole and on which a fitting hole is formed.

According to such a configuration, the length between the insertion member, for example, a luer etc. and the valve can be shortened, and it is possible to easily and reliably disinfect, if necessary, the disc-like valve before and after use. Furthermore, it is advantageous that since the structure is relatively simple, the defective fraction is small and few failures occur.

Furthermore, it is preferable in the mixing/charging port for medical treatment of the present invention that at least two projecting parts are formed on the side surface of the seating and at least two notches engaging the projecting parts are formed on the cover. According to such a configuration, the main body of the mixing/charging port for medical treatment can be fixed reliably to the cover. Moreover, since a solvent such as adhesives etc. is not used when fixing, it is possible to exclude the possibility that the adhesives, etc. may elute into the liquid to be injected or collected.

Furthermore, it is preferable that the mixing/charging port for medical treatment of the present invention further includes a recess part where the valve and the cover can be put in and joined with each other. According to such a configuration, it is possible to anchor the main body of the mixing/charging port reliably to the cover, and also possible to reduce a dead space formed between the bottom surface of the disc-like valve and the passage. The "dead space" herein denotes the space generated between the upper end of the passage and the bottom surface of the disc-like valve.

Furthermore, it is preferable in the mixing/charging port for medical treatment of the present invention that the cover further has a gentle taper on the front surface side. Providing a taper makes it possible to induce the insertion member, for example, a luer, etc. into a fitting hole easily, as well as to wipe out a residual liquid, or to disinfect the mixing/charging port by using an alcohol-impregnated cotton, etc., easily and reliably.

Furthermore, it is desirable in the mixing/charging port for medical treatment of the present invention that a dead space formed between the bottom surface of the valve and the upper end of a passage is 0.05 ml or less. When the dead space is 0.05 ml or more, there is an increased risk that air bubbles are intermixed. Furthermore, the loss of the infused liquid medicine might occur by retention of part of the liquid. In particular, in the mixing/charging port for the liquid infusion, there is a possibility of propagation of bacteria; and in the mixing/charging port for blood transfusion, there is a possibility of clotting of blood.

Furthermore, it is preferable that the mixing/charging port for medical treatment further includes an annular rib formed in an annular form along the edge of the seating on which the hole is provided on the upper part of the seating. According to such a configuration, when the valve is deformed due to the insertion of the insertion member into the mixing/charging port, it is possible to prevent the liquid leakage between the valve and the seating and also to improve the re-closing property of the valve when the insertion member is pulled out and the recovering performance of the valve that caves down. Furthermore, it is desirable that the wall thickness of the edge of the seating on which the hole is provided on the upper part of the seating in the range from 0.3 to 1.0 mm. When the wall thickness is 0.3 mm or less, it is difficult to provide the annular rib; and when it is more than 1.0 mm, the dead space is 0.05 ml or more. Furthermore, it is desirable that the hole provided on the upper part of the seating has a round shape, and the hole diameter is in the range from 5.0 to 8.0 mm. When the diameter is 5.0 mm or less, it is difficult to insert the insertion member; and when it is more than 8.0 mm, the dead space becomes 0.05 ml or more. The most preferable diameter of the hole provided on the upper part of the periphery of the seating is around 6.0 mm.

Furthermore, it is preferable in the mixing/charging port for medical treatment of the present invention that the anchor means is a round fitting hole formed at the center of the cover, and the fitting hole anchors the insertion member by the edge of the cover on which the fitting hole is formed. According to such a configuration, the insertion member easily can be anchored without using an anchor means having a specific mechanism. Furthermore, the insertion member can be anchored penetrating through the disc-like valve. Consequently, it is possible not only to infuse the liquid but also to collect the liquid. Furthermore, it is desirable that the fitting hole has a hole diameter in the range from 3.9 to 4.4 mm and a wall thickness of the part of the cover on which the fitting hole is provided and which is in contact with the insertion member in the range from 0.3 to 1.0 mm. If the ranges do not fall in the above-mentioned ranges, it is difficult to anchor the insertion member. Moreover, the space between the insertion hole or the fitting hole and the valve is increased. Thus, there arise some problems with respect to wiping out of the liquid or sanitary affairs.

Furthermore, it is preferable in the mixing/charging port of the present invention that an annular groove is formed on the surface of the disc-like valve and an annular hook capable of engaging the annular groove is formed on the restrained part of the cover. According to such a configuration, the disc-like valve can be divided into a part compressed and a part stretched by the insertion member, for example, a luer, etc. Thus both the airtightness and operability and re-closing properties can be satisfied at the same time.

Furthermore, it is preferable in the mixing/charging port of the present invention that the outer circumference of the valve has a round shape or an elliptical shape. With such shapes, the insertion member, for example, a luer, etc. easily can be inserted.

Furthermore, it is desirable in the mixing/charging port of the present invention that the insertion hole is a straight slit and the length $L0$ of the slit is in the range from 3.0 to 4.5 mm. When the length is 3.0 mm or less, it is difficult to insert the insertion member, and when the length is more than 4.5 mm, the airtightness is deteriorated when the insertion member is inserted.

Furthermore, it is desirable that the mixing/charging port of the present invention satisfies: $1.1 \leq D2/L0 \leq 4$, wherein $D2$ is an outer diameter of the valve and $L0$ is a length of the slit. When the ratio ($D2/L0$) is less than 1.1, the valve may be deformed or damaged or torn when the insertion member is inserted; and when the ratio is more than 4, the size of the valve is increased. Consequently, the size of the mixing/charging port itself becomes large, and thereby it is difficult to mount the mixing/charging port for medical treatment on a medical instrument.

Furthermore, it is desirable in the mixing/charging port of the present invention that the wall thickness of the valve is in the range from 1.0 to 2.0 mm. It is because the thickness of the valve is preferably made thin in the range in which the liquid does not leak, in order to make it easy to insert the insertion member. Furthermore, it is desirable that the valve is made of an elastic material having a rigidity of 20 to 55 in accordance with JIS-A.

Furthermore, it is desirable in the mixing/charging port of the present invention that the insertion member is fitted penetrating through the valve and the following relation is satisfied: $(L1+L2) \leq D \leq D\text{ max}$, wherein D max is a maximum insertion depth, D is an insertion depth, L1 is a wall thickness of the valve and L2 is a wall thickness of the part of the cover on which the fitting hole is provided and which is in contact with the insertion member. With such a configuration, it is possible not only to hold the insertion member reliably but also to charge and collect the liquid. It is further desirable that the above-mentioned relationship satisfies: $(L1+L2) \leq D \leq 2D\text{ max}/3$.

Furthermore, it is preferable in a mixing/charging port for medical treatment of the present invention that a material of the valve is selected from the group consisting of silicone rubber, natural rubber, synthetic rubber and thermoplastic elastomer. By selecting such a material, it makes it easy to maintain the functions, for example, airtightness, insertion property, re-closing property, and the like.

Furthermore, it is preferable that the mixing/charging port for medical treatment of the present invention further includes a cover holder which has at least two hooks capable of engaging at least two notches provided on the cover and which covers the seating from the lower part, engages the cover covering the seating from the upper part, thereby covering and protecting the seating. It is because there may also be a risk that the projecting part of the mixing/charging port main body is affected and damaged due to the DOP (dioctyl phthalate), etc. from a vinyl chloride tube when the autoclave sterilization is carried out.

Furthermore, it is preferable that the mixing/charging port for medical treatment of the present invention includes at least two projecting parts provided on the side surface of the periphery of the cover and has an anchor means for anchoring the insertion member by using a cylindrical free nut lock having notches engaging the projecting parts, being held with inserted by the insertion member, and inserting the insertion member into the insertion hole while rotating the bottom surface, thereby engaging the notches provided on the bottom surface with the projecting parts of the cover capable of engaging the projecting parts. According to such a configuration, the insertion member can reliably be anchored.

BEST MODE FOR CARRYING OUT THE INVENTION

The mixing/charging port for medical treatment according to the present invention mainly includes a valve opening and closing a passage, a cover restraining the valve, and an anchor means for an insertion member, which is formed on the cover. Hereinafter, each component will be described, respectively.

Figure 1A:
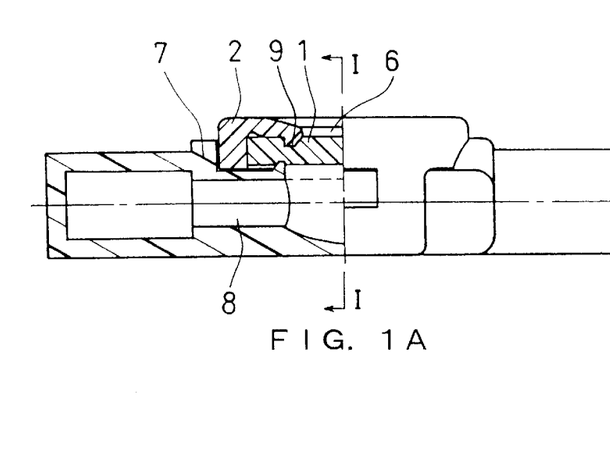
FIG. 1A is a front, partially cross-sectional view showing a mixing/charging port for medical treatment according to the present invention.
Figure 1B:
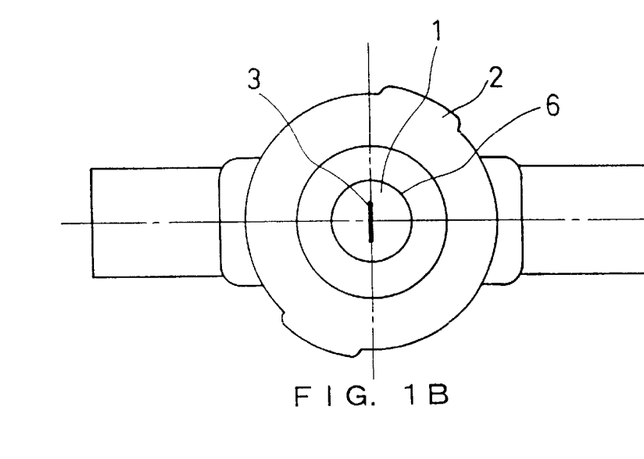
FIG. 1B is a plan view showing a mixing/charging port for medical treatment according to the present invention.
Figure 1C:
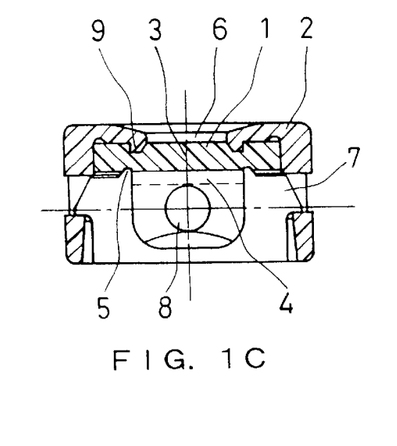
FIG. 1C is a cross-sectional view showing a mixing/charging port for medical treatment according to the present invention.

First, the cover will be explained. There is no particular limitation concerning the shape of the cover. Any shapes may be employed as long as they can tightly hold (restrain) the valve when the insertion member is inserted into and pulled out from the valve. For example, as shown in FIG. 1B, when there is formed a cover 2 covering at least the upper part of the periphery of the valve 1 with the center of the front surface side of the valve 1 left uncovered (open), an insertion site for a luer easily can be spotted and the contamination on the front surface of the valve due to an accidental contact can be prevented. It is more effective that the front surface side of the cover 2 is provided with a gentle taper (tilt). Furthermore, it is preferable to include a seating 7 supporting the lower part of the periphery of the cover 2 or the valve 1 with the center on the rear surface side of the valve 1 left unsupported. It is because the valve 1 can reliably be restrained in the upper and lower parts of the periphery in the mixing/charging port. As shown in FIG. 1C, when an annular rib 5 is provided in an annular form along the edge of the seating on which a hole formed on the upper part of the seating 7, it is possible to prevent the liquid leakage between the valve 1 and the seating 7 even if the valve 1 is deformed due to the insertion into the mixing/charging port. The wall thickness of the edge of the seating on which a hole formed on the upper part of the seating 7 is preferably in the range from 0.3 to 1.0 mm in order to reduce a retention part, i.e., a dead space 4, which is formed between the bottom surface of the valve 1 and the upper end of the inlet port.

Next, the anchor means will be explained. There is no particular limitation concerning the anchor means as long as it anchors the insertion member to the mixing/charging port by a simple structure. An example of such anchor means includes a round fitting hole 6, which is formed at the center of the cover 2 and which has a shape and size so that a fitting hole 6 and the insertion member, for example, a luer, etc. is so fitted to each other as to be capable of anchoring. According to such a configuration, it is possible to anchor the insertion member to the insertion hole and the fitting hole 6 of the cover 2 and it is possible to anchor the insertion member reliably by using a simple structure. When the insertion member is an injector tip having a general luer form and a liquid infusion/blood transfusion set adapter, it is desirable that the diameter of the fitting hole 6 is in the range from 3.9 to 4.4 mm and the wall thickness of the part of the cover on which the fitting hole is provided and which is in contact with the insertion member is in the range from 0.3 to 1.0 mm. Furthermore, it is preferable that the anchor means has such a sufficient strength that the cover 2 is not broken when the insertion member is tightly fitted to the fitting hole 6. In consideration of the chemical resistance, heat resistance, etc, examples of materials for the anchor means include polyvinylacetal, polypropylene, polyamide, polyethylene terephthalate, polybutylene terephthalate, and the like.

Next, the shape, size and material of the disc-like valve 1 will be described. Any types of valves may be used for the valve 1 as long as they have a structure which the insertion member can be inserted into and pulled out from and which is reliably openable and closable. For example, the disc-like valve 1 may have a flat surface. Furthermore, the disc-like valve 1 having a mortar-shaped surface may be employed. The mortar-shaped valve has advantages that the luer, etc. easily can be inserted into and is not likely to be inadvertently pulled out, or the liquid can be prevented from leaking from the insertion hole when the insertion member is pulled out. However, it has a practical shortcoming that residual liquid is generated on the disc-like valve 1 and not easily wiped out.

Furthermore, it is convenient that the outside shape of the valve 1 is round or elliptic for forming the mixing/charging port. It is simple and easy that the insertion hole 3 is a straight slit. When the insertion member has a general luer form as mentioned above, the length L0 of the slit is preferably in the range from 3.0 to 4.5 mm with respect to the insertion property of the valve 1 or liquid tightness. Furthermore, it is preferable that the ratio (D2/L0) of the outer diameter D2 of the valve 1 to the length L0 of the slit satisfies: $1.1 \leq D2/L0 \leq 4$ for the below mentioned reasons. It is preferable that the wall thickness of the valve 1 is in the range from 1 to 2 mm with respect to the insertion property, backflow prevention effect, cost efficiency, etc. A material for the valve 1 is not particularly limited and any rubber elastic materials may be used. More specifically, a rubber material having a rigidity of 20 to 55 in accordance with JIS-A is more preferable. Specific materials include silicone rubber, natural rubber, synthetic rubber such as butyl rubber, nitrile rubber, etc., thermoplastic elastomer, or the like.

Hereinafter, the mixing/charging port for medical treatment according to the embodiment of the present invention will be explained with reference to drawings. FIG. 1A is a front, partially cross-sectional view showing a mixing/charging port for medical treatment according to the present invention; FIG. 1B is a plan view showing the same; and FIG. 1C is a cross-sectional view showing the same, respectively. In FIGS. 1A to C, reference numeral 1 denotes a disc-like valve, 2 denotes a cover and 3 denotes an insertion hole.

Figure 2A:
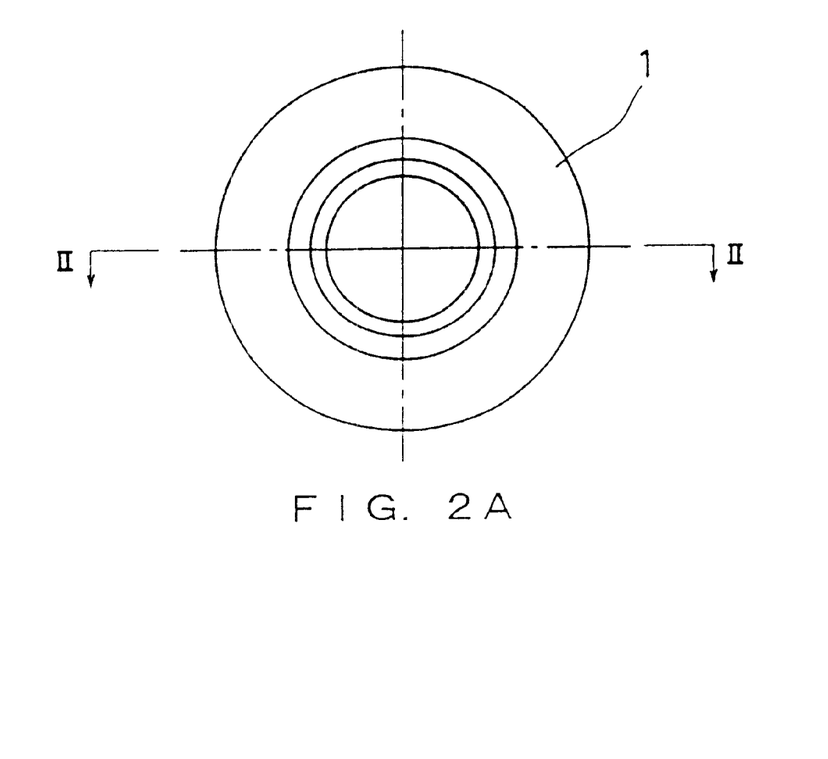
FIG. 2A is a plan view showing a disc-like valve of the mixing/charging port for medical treatment according to the present invention.
Figure 2B:
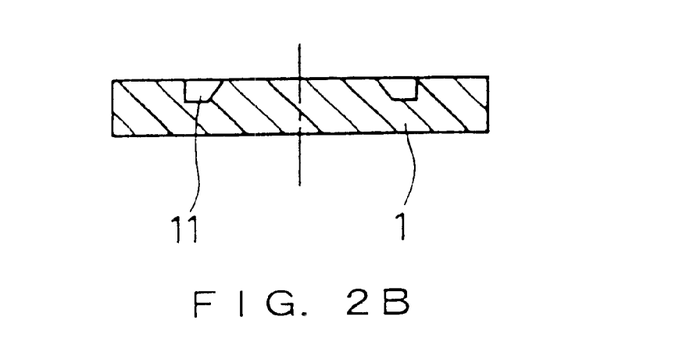
FIG. 2B is a cross-sectional view showing a disc-like valve of the mixing/charging port for medical treatment according to the present invention.

As shown in FIG. 2A and FIG. 2B, the valve 1 has a flat surface and an annular notch 11 on the surface. The notch 11 engages a hook 9 of the cover 2, thereby dividing the disc-like valve into the stretching part and the compressed part. In other words, the valve 1 is fixed with also the hook 9. Therefore, when the insertion member is inserted into the valve 1, the valve 1 is stretched between the insertion hole 3 (slit) and the hook 9, but compressed in the part outward of the hook 9. When the hook 9 is not provided, after the insertion member is pulled out, the returning performance of the valve 1 is inhibited by the compressive power used for maintaining the airtightness of the holding part of the periphery of the valve 1, so that the insertion hole 3 cannot return to the original state. That is, the valve caves in downward (warps). Thereby, the fact that the above-mentioned cave-in state is not recover to the normal state may cause some problems in terms of contamination, liquid residual, airtightness, and the like. However, by dividing the valve 1 into the stretching part and compressed part by providing the hook 9, it is possible to maintain the airtightness in the compressed part as conventionally. Furthermore, the valve 1 easily can return to the original state in the stretching part. Thus, returning to the normal state can also be attained at the same time. Furthermore, since the insertion member is inserted into the valve while being guided by the hook 9, it is possible to improve the easiness of insertion and fitting property when the insertion member is inserted into the slit.

Figure 3A:
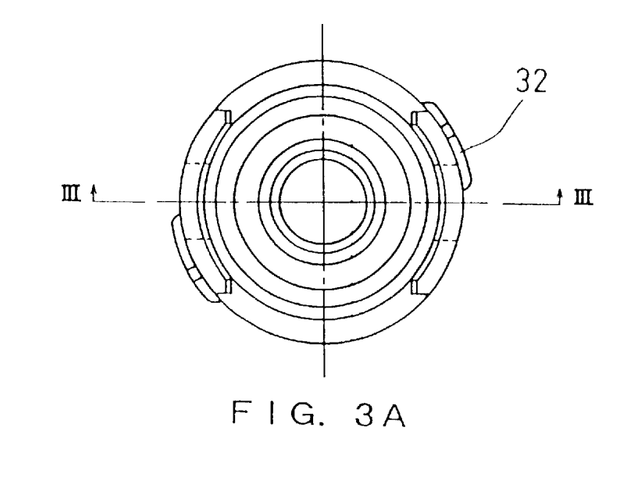
FIG. 3A is a plan view showing a cover of the mixing/charging port for medical treatment according to the present invention.
Figure 3B:
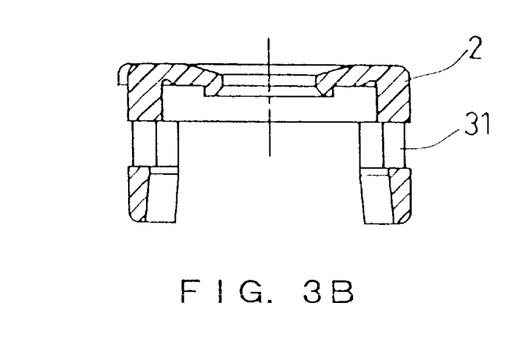
FIG. 3B is a cross-sectional view showing a cover of the mixing/charging port for medical treatment according to the present invention.
Figure 3C:
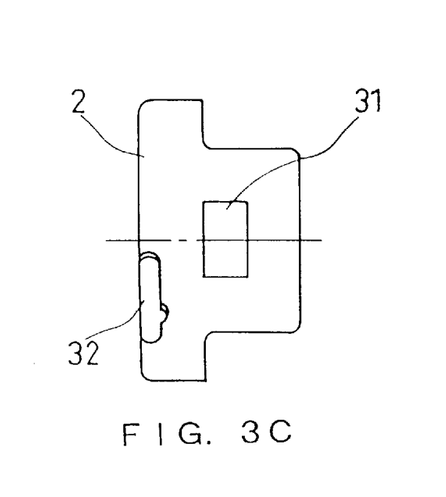
FIG. 3C is a side view showing a cover according to the present invention.

As shown in FIGS. 3A to 3C, the cover 2 has a fitting hole at the center and a gentle taper (tilt) toward the fitting hole. Furthermore, the cover 2 has at least two notches 31 on the outer side, and the notches 31 engage projecting parts provided on the side surface of the main body of the mixing/charging port, so that the cover 2 can be fitted to the main body outside the mixing/charging port.

Figure 4:
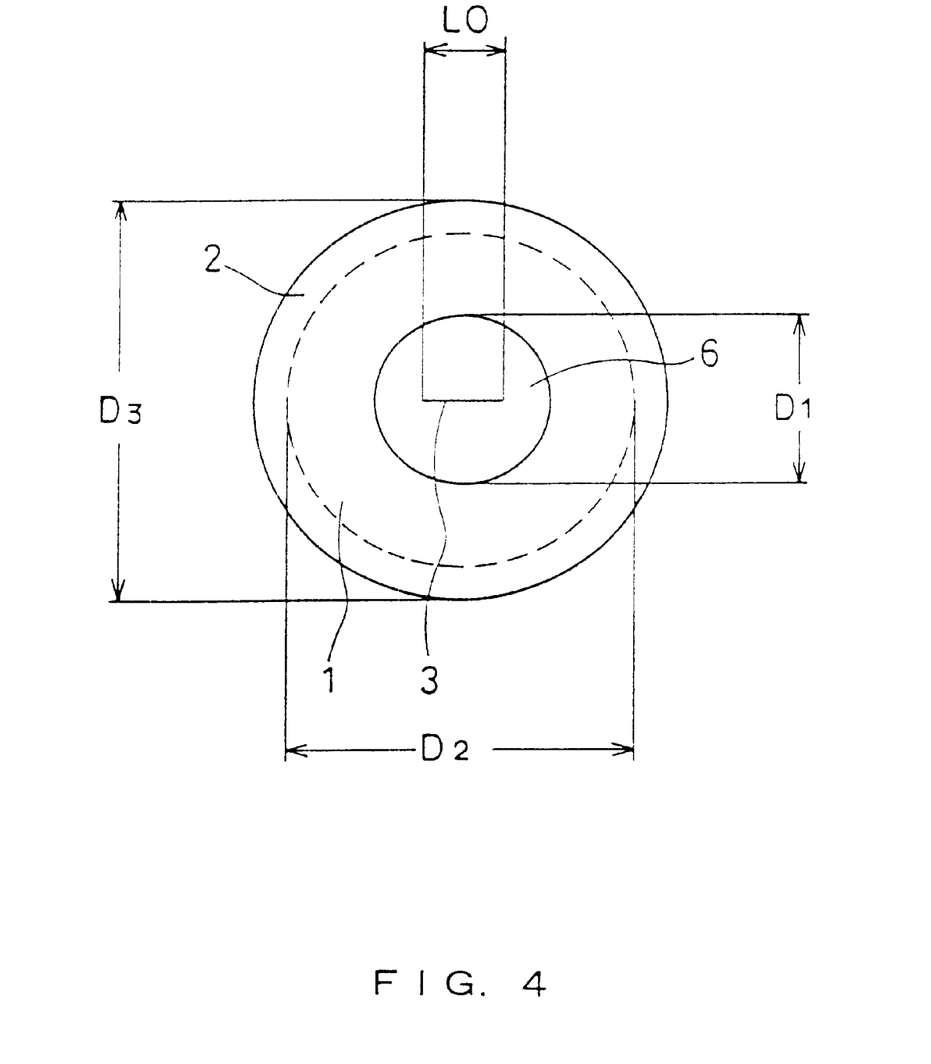
FIG. 4 is a plan view showing a mixing/charging port for medical treatment according to the present invention.

The insertion hole 3 may be one straight slit or three straight silts, intersecting with each other in the center. FIG. 4 is a plan view showing a mixing/charging port for medical treatment of the embodiment according to the present invention seen from the direction in which the insertion member, for example, a luer etc. is inserted. In FIG. 4, the outer shape of the cover 2 is round, however, similar to the shape of the valve, it may be an elliptic shape. The cover 2 covers and restrains the periphery and the upper part of the periphery of the valve 1 with the center of the valve 1 uncovered and unrestrained. Thereby, it is possible to reduce the surface, which is exposed to the outer world, of the insertion hole of the mixing/charging port for medical treatment and thus to reduce the opportunity of infection. Furthermore, with this cover, the insertion member inserted into the disc-like valve 1 can be held tightly in the mixing/charging port for medical treatment. For example, when the center of the cover is provided with a round fitting hole 6 having a diameter equal to or slightly smaller than that of the insertion member, the insertion member such as a conduit, a luer, etc, which is inserted into the valve, can be held tightly by fitting them in the fitting hole 6. When only by inserting the insertion member into the valve 1, the insertion member cannot be held stably. Furthermore, there is a risk that the insertion member being inserted into the valve for a long time is urged back by the elastic disc-like valve 1 and pulled out from the valve 1. However, in this embodiment, the insertion member is tightly held, and thus the above-mentioned a risk can be avoided.

The shape and size of the fitting hole 6 may be adjusted in accordance with kinds of insertion members. When an injector, an infusion/transfusion set, and the like, are frequently connected to the mixing/charging port, it is preferable that the size is determined so as to be adjusted to the standard luer size, and that the diameter is in the range from 3.9 to 4.4 mm, and the wall thickness is in the range from 0.3 to 1.0 mm, more preferably the diameter is in the range from 3.9 to 4.2 mm and the wall thickness is in the range from 0.5 to 0.7 mm. Furthermore, the fitting hole 6 may be formed in a taper shape by corresponding to the shape of the above-mentioned insertion member, i.e., a tapered luer. Materials for the cover 2 of the mixing/charging port need to have suitable rigidity for tightly holding the valve 1 or the insertion member. In particular, it is desirable that the cover 2 has a suitable rigidity (too much rigidity reduces its capability for accepting the insertion member) so that the insertion member easily can be inserted into and also be tightly fitted to the fitting hole 6. It is also desirable that the cover 2 is formed of a material that is not likely to be fractured. The desirable examples of such materials include polyacrylamide, polyethylene terephthalate, polybutylene terephthalate, and the like, in addition to polyvynilacetal and polypropylene.

Figure 5:
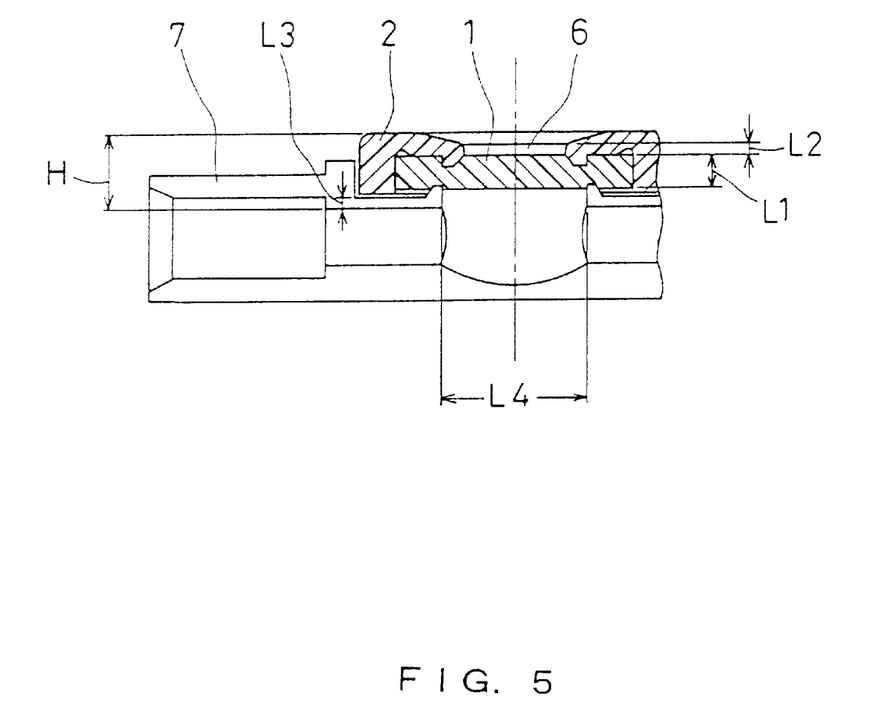
FIG. 5 is a cross-sectional view showing a mixing/charging port for medical treatment according to the present invention.

Furthermore, as shown in FIG. 1C, when the cover 2 is provided with a seating 7 supporting the lower part of the periphery of the valve 1 with the center of the rear side surface of the valve 1 left unsupported, the valve 1 can be restrained tightly by the main body of the mixing/charging port for medical treatment. The seating 7 is formed in an annular shape in accordance with the shape of the valve. As shown in FIG. 5, it is desirable that the wall thickness L3 of the tip of the seating 7 (the side edge of the innermost circumference of the seating 7) is in the range from 0.1 to 1.0 mm, more desirably in the range from 0.3 to 0.7 mm for miniaturizing the retention part (dead space) 4 of the lower part of the valve while restraining the valve 1. Furthermore, as shown in FIG. 1C or FIG. 5, the annular rib 5 is formed on the edge of the seating 7 on which a hole is formed on the upper part of the seating 7, that is the lower edge of the valve, which is in contact with the periphery of the valve, and even if the valve is deformed when it is inserted into the mixing/charging port, it is possible to prevent the liquid from leaking from the inside of the mixing/charging port through between the valve 1 and the seating 7. It is preferable that the rib is formed in an annular shape along the edge of the seating on which the hole is provided on the upper part of the seating 7 as the annular rib 5 of the mixing/charging port shown in FIG. 5 with respect to the easy formation, securing of the re-closing property, prevention of cave-in, prevention of liquid leaking, and the like.

As shown in FIG. 4, D1 denotes a diameter of the fitting hole 6, D2 denotes an outer diameter of the disc-like valve 1, and L0 denotes a length of the slit of the insertion hole 3. At this time, it is preferable that the relation: $1.1 \leq D2/L0 \leq 4$ is satisfied with respect to the insertion property of the valve, backflow prevention effect, or the like. When the length L0 of the insertion hole is larger than the outer diameter D2 of the valve, namely, D2/L0 is less than 1.1, the valve maybe deformed or damaged (torn) when the insertion member is inserted into the valve. Furthermore, since the deformable part of the periphery of the valve is smaller with respect to the insertion hole 3 (when the insertion member is inserted into the valve), it becomes difficult to insert the insertion member into the valve. On the contrary, when the D2/L0 is more than 4, the insertion member is easily inserted into the valve, but the mixing/charging port becomes larger, thus causing the cost to increase. Furthermore, it is difficult to mount the mixing/charging port on the medical equipment. The length L0 of the slit that is an insertion hole and the insertion member will be described. It is preferable that the length L0 of the slit is 0.7 times or more and 1.1 times or less than an insertion part diameter. The insertion part diameter is herein defined as a diameter of the part of the insertion member buried in the valve when the insertion member is inserted into the slit. When L0 is smaller than the above range, it is difficult to insert the insertion member into the valve. On the other hand, when L0 is larger than the above range, liquid easily leaks from the insertion hole when the insertion member is pulled out from the mixing/charging port.

It is preferable that the wall thickness L1 of the valve shown in FIG. 5 is in the range from 1 to 2 mm with respect to the insertion property, backflow prevention effect, cost efficiency, etc. As a material for the valve 1, any materials may be employed as long as they are general rubber elastic materials. More specifically, a rubber material having a rigidity of 20 to 55 in accordance with JIS-A. Specific materials include a silicone rubber, a natural rubber, a synthetic rubber such as butyl rubber, nitrile rubber, etc., thermoplastic elastomer, or the like.

Figure 11:
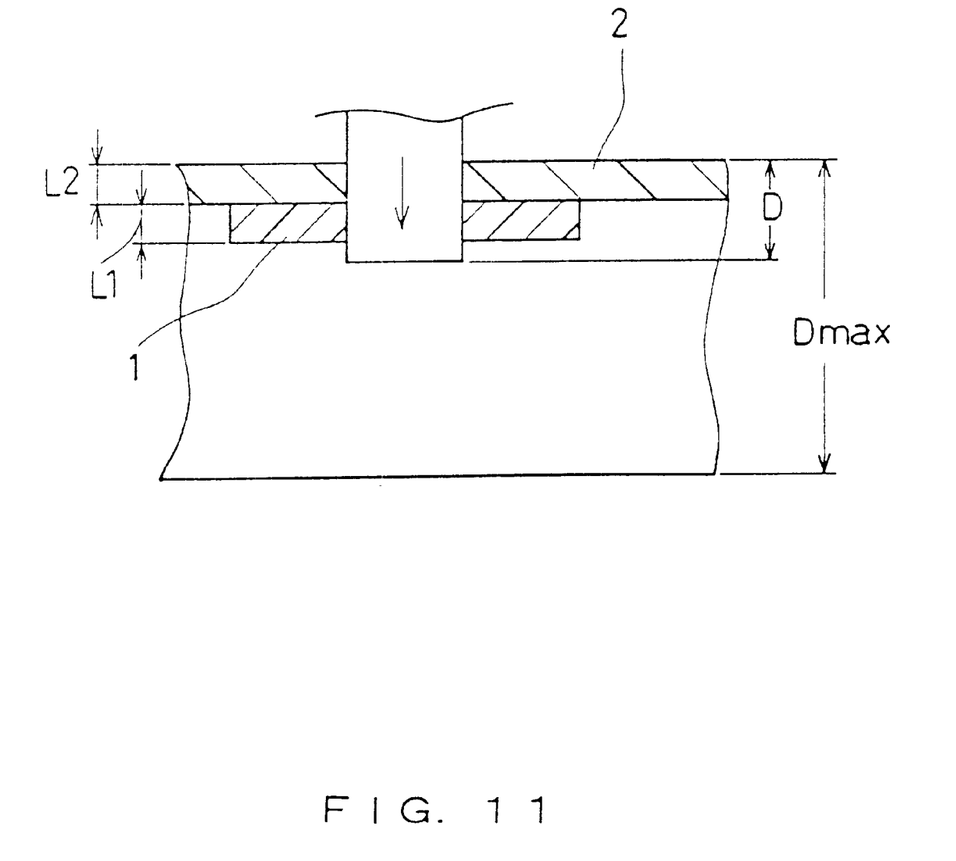
FIG. 11 is a view explaining a state in which the insertion member is inserted.

As shown in FIG. 11, the insertion member needs to be held penetrating through the valve 1, in order to enable not only the liquid infusion from the mixing/charging port but also collecting of the liquid from the mixing/charging port. That is, it is necessary to satisfy the following relation: $(L1+L2) \leq D \leq D$ max, where D is an insertion depth, D max is the maximum value of the insertion depth, namely, the depth to the bottom surface of the mixing/charging port, L1 is a wall thickness of the valve and L2 is a wall thickness of the part of the cover on which the fitting hole is provided and which is in contact with the insertion member. In fact, even when the insertion member is in close contact with the bottom surface of the mixing/charging port main body, if the contact surface is not a flat surface but a rough surface, it is possible to infuse and collect liquid. However, it is desirable that the relation: $(L1+L2) \leq D \leq 2D$ max/3 is satisfied.

Figure 6A:
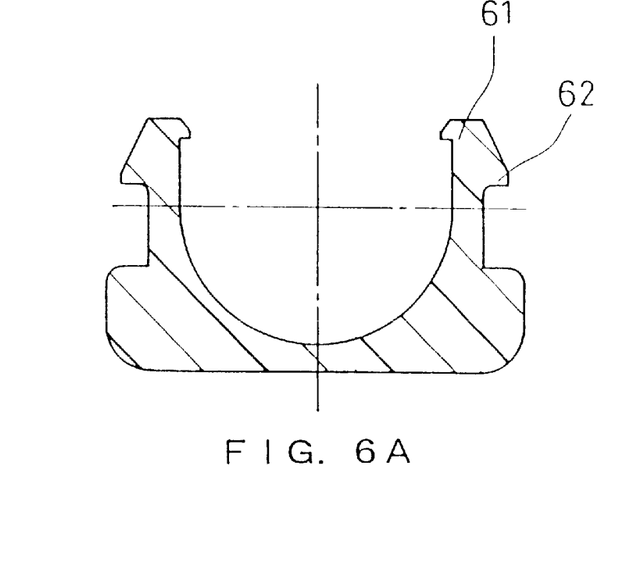
FIG. 6A is a cross sectional view showing a holder of the mixing/charging port for medical treatment according to the present invention.
Figure 6B:
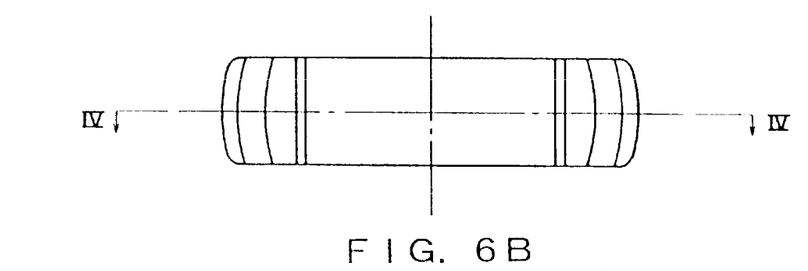
FIG. 6B is a plan view showing a holder of the mixing/charging port for medical treatment according to the present invention.
Figure 6C:
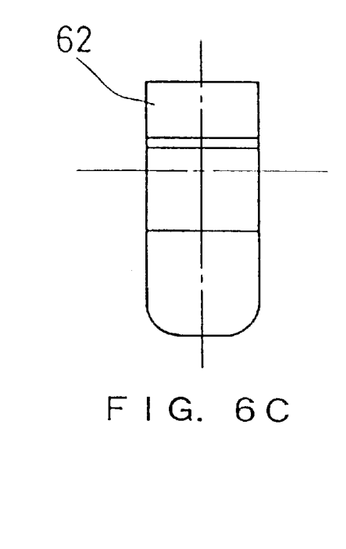
FIG. 6C is a side view showing a holder of the mixing/charging port for medical treatment according to the present invention.
Figure 7A:
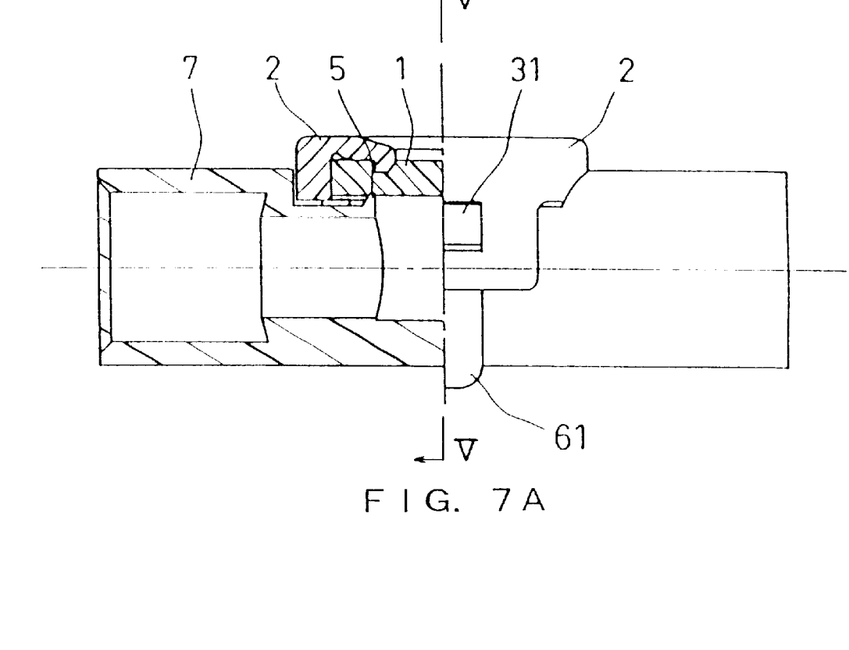
FIG. 7A is a front, partially cross-sectional view showing the mixing/charging port for medical treatment according to the present invention when the holder is used.
Figure 7B:
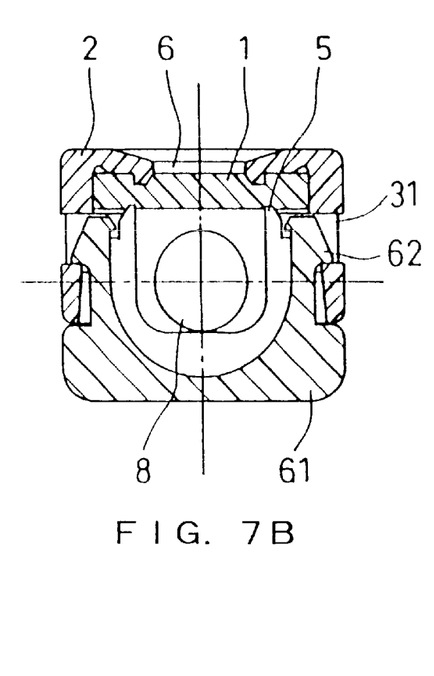
FIG. 7B is a cross-sectional view showing the mixing/charging port for medical treatment according to the present invention when the holder is used.
Figure 8A:
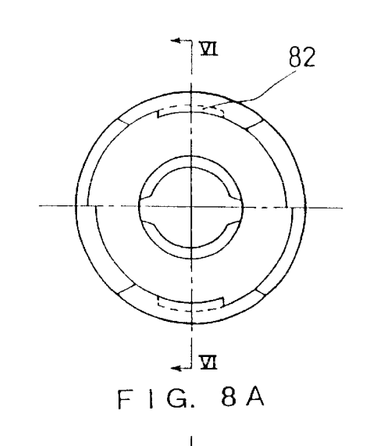
FIG. 8A is a bottom view showing a free nut lock of the mixing/charging port for medical treatment according to the present invention.
Figure 8B:
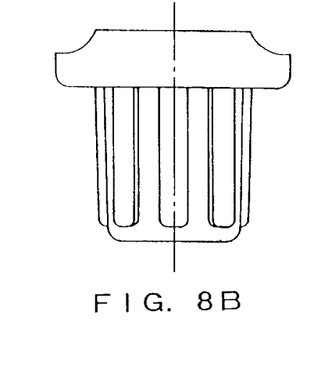
FIG. 8B is a side view showing a free nut lock of the mixing/charging port for medical treatment according to the present invention.
Figure 8C:
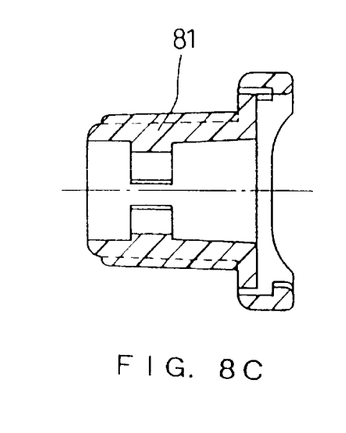
FIG. 8C is a cross-sectional view explaining a free nut lock of the mixing/charging port for medical treatment according to the present invention.
Figure 8D:
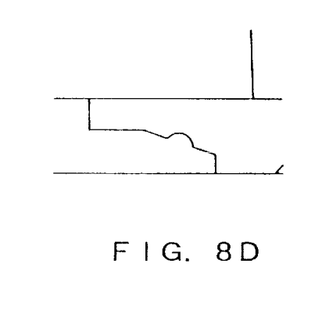
FIG. 8D is a view showing a state in which a free nut lock is connected in the mixing/charging port for medical treatment according to the present invention.

Next, when the mixing/charging port according to the present invention is used for a blood circuit, it is effective further to add a cover holder 61 capable of engaging the cover 2 as shown in FIGS. 6A to C to the outside. For a material of the mixing/charging port main body, polycarbonate is employed in consideration of the securing of transparency and adhesive property of a tube. Therefore, the mixing/charging port is poor in the chemical resistance. Consequently, the projecting part formed on the mixing/charging port main body may be affected and damaged by DOP (dioctyl phthalate), and the like, from a vinyl chloride tube during the autoclave sterilization. In order to prevent such a risk beforehand, as shown in FIGS. 7A and 7B, the mixing/charging port is provided with a cover holder 61 made of a different material so as to cover the outside of the mixing/charging port main body, and the hook 62 on the upper part of the cover holder 61 and the notch 31 of the cover 2 are engaged and fixed.

Figure 9:
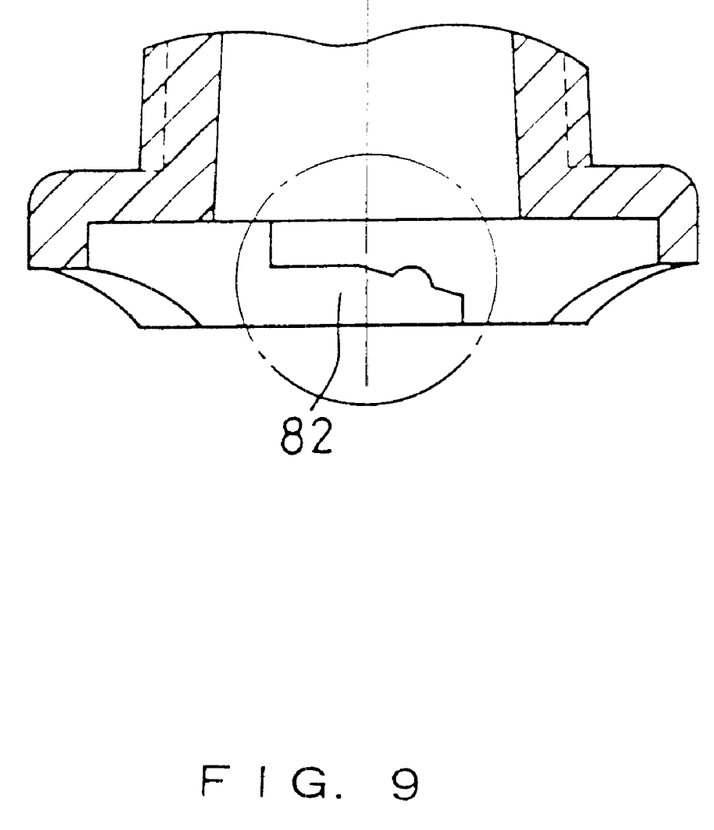
FIG. 9 is an enlarged view of the connection part of a lock adapter cap cover.
Figure 10A:
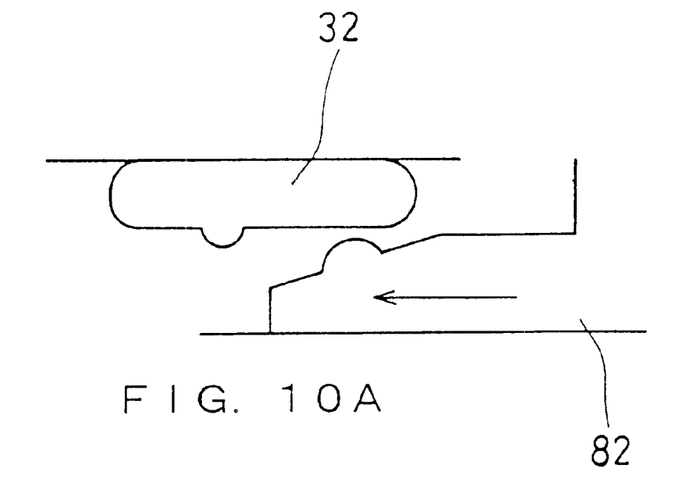
FIG. 10A is a view explaining a state of the lock adapter cap cover before connecting.
Figure 10B:
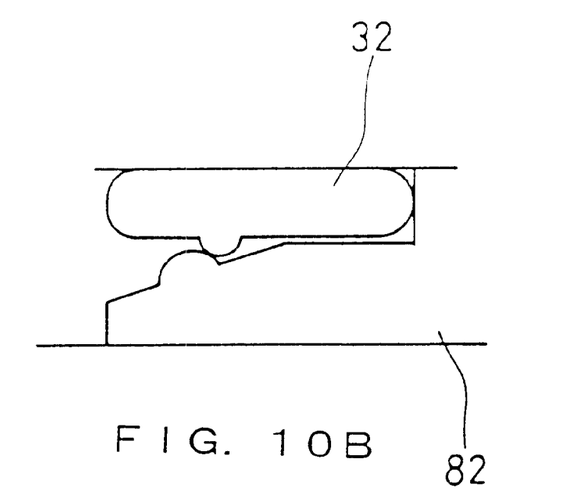
FIG. 10B is a view explaining a state in which the lock adapter cap cover is connected.

Furthermore, in order to anchor the insertion member more reliably, it is also effective to use a free nut lock shown in FIGS. 8A to 8D. A lock adapter cap cover 81 is rotatable and is fixed to the cover 2 by the use of a notch 82 provided in the lower part. That is, FIG. 9 is an enlarged cross-sectional view showing the lower part of the lock adapter cap cover 81. The inner side of the lock adapter cap cover 81 has the notch 82 capable of rotating and engaging. As shown in FIG. 10A, the lock adapter cap cover 81 is put in so that the notch 82 is fitted to the projecting part 32 located on the periphery of the cover, and then rotated, thus engaging and reliably fixing thereof as shown in FIG. 10B.

INDUSTRIAL APPLICABILITY

As mentioned above, in the mixing/charging port of the present invention, once the insertion member is connected to the mixing/charging port, the insertion member can be held reliably without being inadvertently pulled out.

Furthermore, since the mixing/charging port has the insertion member and simple anchor means, the shape and size of the mixing/charging port valve and the mixing/charging receiving part is less restrained. Consequently, the designing of the whole mixing/charging port is relatively free. Therefore, it is possible to select a preferable shape and size in terms of sanitary effect and the functions. As a result, the mixing/charging port of the present invention can reduce the opportunity of contamination.

Furthermore, the insertion member is maintained in a state in which it is inserted into the valve and a passage is secured. Thus, there is no possibility of occurrence of the waste of administered liquid medicine. Furthermore, since the mixing/charging port has a simple structure, it can be manufactured at low cost, and can be mounted on various kinds of medical instruments.

What is claimed is:

1. A mixing/charging port for medical treatment comprising
   a disc-like valve having an insertion hole at the center,
   a seating for supporting a lower part of the periphery of the valve with the center of a lower surface side of the valve,
   a cover for restraining the valve by covering at least an upper part of the periphery of the valve with the center on the upper surface side of the valve left uncovered, and
   an anchor means for anchoring an insertion member to the mixing/charging port by using the edge of the cover which is adapted to insert an insertion member into an insertion hole and on which a fitting hole is formed,
   wherein a wall defining the fitting hole has a thickness in the range from 0.3 to 1.0 mm.

2. The mixing/charging port for medical treatment according to claim 1, wherein at least two projecting parts are formed on a side surface of the seating and at least two notches engaging the projecting parts are formed on the cover.

3. The mixing/charging port for medical treatment according to claim 1, further comprising a recess part where the valve and the cover can be inserted in and joined with each other.

4. The mixing/charging port for medical treatment according to claim 1, wherein the cover further has a taper on the upper surface side thereof.

5. The mixing/charging port for medical treatment according to claim 1, wherein a dead space formed between the bottom surface of the valve and an upper end of a passage is 0.05 ml or less.

6. The mixing/charging port for medical treatment according to claim 1, further comprising an annular rib formed in an annular form along an edge of the seating on which the hole is provided on an upper part of the seating.

7. The mixing/charging port for medical treatment according to claim 1, wherein a wall thickness of an edge of the seating on which the fitting hole is provided on the upper part of the seating is in the range from 0.3 to 1.0 mm.

8. The mixing/charging port for medical treatment according to claim 1, wherein the fitting hole provided on the upper part of the seating has a round shape, and the hole diameter is in the range from 5.0 to 8.0 mm.

9. The mixing/charging port for medical treatment according to claim 1, wherein the anchor means is a round fitting hole formed at the center of the cover.

10. The mixing/charging port for medical treatment according to claim 8, wherein the fitting hole has a hole diameter in the range from 3.9 to 4.4 mm.

11. The mixing/charging port for medical treatment according to claim 1, wherein an annular groove is formed on a surface of the disc-like valve and an annular hook capable of engaging the annular groove is formed on a restrained part of the cover.

12. The mixing/charging port for medical treatment according to claim 1, wherein the outer circumference of the valve has a round shape or an elliptical shape.

13. The mixing/charging port for medical treatment according to claim 1, wherein the insertion hole is a straight slit and a length L0 of the slit is in the range from 3.0 to 4.5 mm.

14. The mixing/charging port for medical treatment according to claim 13, satisfying:

$$1.1 \leq D2/L0 \leq 4,$$

wherein D2 is an outer diameter of the valve.

15. The mixing/charging port for medical treatment according to claim 1, wherein a wall thickness of the valve is 1.0 to 2.0 mm.

16. The mixing/charging port for medical treatment according to claim 15, wherein the valve is made of an elastic material having a rigidity of 20 to 55 in accordance with JIS-A.

17. The mixing/charging port for medical treatment according to claim 17, wherein a material of the valve is selected from the group consisting of silicone rubber, natural rubber, synthetic rubber and thermoplastic elastomer.

18. The mixing/charging port for medical treatment according to claim 1, wherein the insertion member is fitted so as to penetrate through the valve and the following relation is satisfied:

$$(L1+L2) \leq D \leq D\ \text{max},$$

wherein D max is a maximum insertion depth, D is an insertion depth, L1 is the wall thickness of the valve and L2 is a wall thickness of the fitting hole is formed and which is in contact with the insertion member.

19. The mixing/charging port for medical treatment according to claim 1, further comprising a cover holder which has at least two hooks capable of engaging at least two notches provided on the cover and which covers the seating and engages the cover thereby covering and protecting the seating.

20. The mixing/charging port for medical treatment according to claim 1, which comprises at least two projecting parts provided on a side surface of the periphery of the cover and which has an anchor means for anchoring the insertion member by using a free nut lock having notches capable of engaging the at least two projecting parts.

* * * * *

UNITED STATES PATENT AND TRADEMARK OFFICE
CERTIFICATE OF CORRECTION

PATENT NO.     : 6,468,251 B1
DATED          : October 22, 2002
INVENTOR(S)    : Yamanaka et al.

It is certified that error appears in the above-identified patent and that said Letters Patent is hereby corrected as shown below:

<u>Title page,</u>
Item [73], Assignee, "Jims Co., Ltd." should read -- JMS Co., Ltd. --

Signed and Sealed this

Nineteenth Day of August, 2003

JAMES E. ROGAN
*Director of the United States Patent and Trademark Office*